United States Patent
Brown (10) Patent No.: US 9,644,053 B2
(45) Date of Patent: May 9, 2017

(54) TRIDENTATE NITROGEN BASED LIGANDS FOR OLEFIN POLYMERISATION CATALYSTS

(71) Applicant: Univation Technologies, LLC, Houston, TX (US)

(72) Inventor: Steven D. Brown, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 14/775,757

(22) PCT Filed: Jan. 28, 2014

(86) PCT No.: PCT/US2014/013375
§ 371 (c)(1),
(2) Date: Sep. 14, 2015

(87) PCT Pub. No.: WO2014/143421
PCT Pub. Date: Sep. 18, 2014

(65) Prior Publication Data
US 2016/0024237 A1    Jan. 28, 2016

Related U.S. Application Data

(60) Provisional application No. 61/790,894, filed on Mar. 15, 2013.

(51) Int. Cl.
  *C08F 4/64*      (2006.01)
  *C08F 4/642*     (2006.01)
  *C08F 10/02*     (2006.01)
  *C08F 210/02*    (2006.01)
  *C08F 210/16*    (2006.01)
  *C08F 10/00*     (2006.01)
  *C07C 209/10*    (2006.01)
  *C07C 209/22*    (2006.01)
  *C07C 221/00*    (2006.01)
  *C07F 7/00*      (2006.01)

(52) U.S. Cl.
  CPC .......... *C08F 210/16* (2013.01); *C07C 209/10* (2013.01); *C07C 209/22* (2013.01); *C07C 221/00* (2013.01); *C07F 7/00* (2013.01); *C08F 4/64148* (2013.01); *C08F 10/00* (2013.01); *C08F 10/02* (2013.01)

(58) Field of Classification Search
  CPC ..... C08F 4/64148; C08F 10/02; C08F 210/02
  See application file for complete search history.

(56) References Cited

U.S. PATENT DOCUMENTS

| | | |
|---|---|---|
| 3,412,130 A | 11/1968 | Gustav et al. |
| 6,271,325 B1 | 8/2001 | McConville et al. |
| 8,378,029 B2 | 2/2013 | Liu et al. |
| 2002/0161141 A1 | 10/2002 | Mawson et al. |
| 2015/0166699 A1 | 6/2015 | Kao et al. |

FOREIGN PATENT DOCUMENTS

WO    2004106390    12/2004

OTHER PUBLICATIONS

International Search Report and Written Opinion for related PCT Application PCT/US2014/013375, mailed Mar. 14, 2014 (11 pgs).

*Primary Examiner* — Caixia Lu
(74) *Attorney, Agent, or Firm* — Brooks, Cameron & Huebsch, PLLC (57) ABSTRACT

Catalyst systems and methods for making and using the same are provided. A method for forming a polymer catalyst includes reacting a bromoketone compound with an aryl amine compound to form an amide compound. The amide compound is reacted with an ethylene diamine compound, to form a terminal primary amine compound. The terminal primary amine compound is reacted with a bromoaryl compound to form a ligand.

16 Claims, 4 Drawing Sheets

TRIDENTATE NITROGEN BASED LIGANDS FOR OLEFIN POLYMERISATION CATALYSTS

This application is a National Stage Application under 35 U.S.C. §371 of International Application Number PCT/US2014/013375, filed Jan. 28, 2014 and published as WO 2014/143421 on Sep. 18, 2014, which claims the benefit to U.S. Provisional Application 61/790,894, filed Mar. 15, 2013, the entire contents of which are incorporated herein by reference in its entirety.

BACKGROUND

Ethylene alpha-olefin (polyethylene) copolymers are typically produced in a low pressure reactor, utilizing, for example, solution, slurry, or gas phase polymerization processes. Polymerization takes place in the presence of catalyst systems such as those employing, for example, a Ziegler-Natta catalyst, a chromium based catalyst, a metallocene catalyst, or combinations thereof.

A number of catalyst compositions containing single site, e.g., metallocene, catalysts have been used to prepare polyethylene copolymers, producing relatively homogeneous copolymers at good polymerization rates. In contrast to traditional Ziegler-Natta catalyst compositions, single site catalyst compositions, such as metallocene catalysts, are catalytic compounds in which each catalyst molecule contains one or only a few polymerization sites. Single site catalysts often produce polyethylene copolymers that have a narrow molecular weight distribution. Although there are single site catalysts that can produce broader molecular weight distributions, these catalysts often show a narrowing of the molecular weight distribution (MWD) as the reaction temperature is increased, for example, to increase production rates. Further, a single site catalyst will often incorporate comonomer among the molecules of the polyethylene copolymer at a relatively uniform rate.

It is generally known in the art that a polyolefin's MWD will affect the different product attributes. Polymers having a broad molecular weight distribution may have improved physical properties, such as stiffness, toughness, processability, and environmental stress crack resistance (ESCR), among others.

To achieve these properties, bimodal polymers have become increasingly important in the polyolefins industry, with a variety of manufacturers offering products of this type. Whereas older technology relied on two-reactor systems to generate such material, advances in catalyst design and supporting technology have allowed for the development of single-reactor bimetallic catalyst systems capable of producing bimodal high density polyethylene (HDPE). These systems are attractive both from a cost perspective and ease of use.

Control of these properties is obtained for the most part by the choice of the catalyst system. Thus, the catalyst design is important for producing polymers that are attractive from a commercial standpoint. Because of the improved physical properties of polymers with the broad molecular distributions needed for commercially desirable products, there exists a need for controlled techniques for forming polyethylene copolymers having a broad molecular weight distribution.

SUMMARY

An embodiment described herein provides a method for forming a polymer catalyst. The method includes reacting a bromoketone compound with an aryl amine compound to form an amide compound. The amide compound is reacted with an ethylene diamine compound, to form a terminal primary amine compound. The terminal primary amine compound is reacted with a bromoaryl compound to form a ligand.

Another embodiment provides a method for generating a polyethylene polymer, including reacting at least ethylene with a catalyst system including a non-metallocene polymerization catalyst formed by: reacting a bromoketone compound with an aryl amine compound to form a substituted amide compound; reacting the amide compound with an ethylene diamine compound, forming a terminal primary amine compound; and reacting the terminal primary amine compound with a bromoaryl compound to form a ligand. The ligand is reacted with a metal compound to form a catalyst precursor and the catalyst precursor is activated to form an active catalyst. The catalyst is reacted with at least ethylene to form a polymer.

Another embodiment provides a polymerization catalyst system that includes a non-metallocene catalyst formed by: reacting a bromoketone compound with an aryl amine compound to form a substituted amide compound; reacting the amide with an ethylene diamine compound, forming a terminal primary amine compound; and reacting the terminal primary amine compound with a bromoaryl compound to form a ligand. The ligand is reacted with a metal center to form a catalyst precursor and catalyst precursor is activated to form an active catalyst.

DETAILED DESCRIPTION

A catalyst support impregnated with multiple catalysts may be used to form polymeric materials with improved balance of properties, such as stiffness, toughness, processability, and environmental stress crack resistance, can be achieved, for example, by controlling the amounts and types of catalysts present on the support. Appropriate selection of the catalysts and ratios may be used to adjust the combined molecular weight distribution (MWD) of the polymer produced. The MWD can be controlled by combining catalysts with the appropriate weight average molecular weight (Mw) and individual molecular weight distributions. For example, the typical MWD for linear metallocene polymers is 2.5-3.5. Blend studies indicate it would be desirable to broaden this distribution by employing mixtures of catalysts that each provides different average molecular weights. The ratio of the Mw for a low molecular weight component and a high molecular weight component would be between 1:1 and 1:10, or about 1:2 and 1:5.

Each of the catalysts can be selected to contribute a certain molecular weight component. For example, a non-metallocene, such as the catalyst shown in structure (I) may be selected to produce a higher molecular weight component. A metallocene may then be selected to produce a low molecular weight component, wherein, for example, a first metallocene catalyst, shown in structure (II), may be selected for resins to be used for film and blow-molding applications, while another metallocene catalyst, shown in structure (III), may be selected for resins to be used for pipe applications. Other metallocenes, as described herein, may be selected for other types of applications. The individual molecular weight components form a single molecular weight distribution (MWD) for the polymer. The non-metallocene (I) and metallocenes (II and III) are not limited to the formulas shown, but may include any number of other catalyst systems.

(I)

(II)

(III)

Embodiments described within present a new methodology for the preparation of catalysts similar to structure (I), herein termed HN5-N type derivatives, which allows multiple points of diversification. The methodology is shown by the general reaction sequence shown in scheme (1):

(1)

In the first step of scheme (1), a bromoketone compound is reacted with an aryl amine compound in a first step to form a substituted amide compound. As shown in the second step of scheme (1) above, the amide compound is reacted with an ethylene diamine compound to form a tri-amine compound featuring a terminal primary amine. Although the ethylene diamine compound is shown as unsubstituted in scheme (1), there may be substituents on either of the two carbons, such as methyl groups, ethyl groups, phenyl groups, and the like. In the third step shown, the terminal primary amine compound is reacted with a bromoaryl compound to form a ligand. In scheme (1), R is an aryl group, a substituted aryl group, or an alkyl group comprising 2 to 20 carbons. Ar is an aryl group or a substituted aryl group and Ar' is an aryl group or a substituted aryl group.

The ligand can then be reacted with a metal compound to form a catalyst precursor, according to scheme (2).

(2)

In scheme (2), M is a Group 3 to 12 transition metal or a Group 13 or 14 main group metal, or a Group 4, 5, or 6 metal. Each X individually is a hydride, a methyl group, an alkyl group, a benzyl group, a chloro group, a bromo group, a fluoro group, or an iodo group. R, Ar, Ar', and X are as described with respect to scheme (1).

This method shown in scheme (1) avoids the use of more traditional and toxic nitrogenous building blocks such as cyanide. It can be noted that the methodology is not limited to the exemplary reagents shown above. For example, any number of similar compounds may replace the Ti(O$^i$Pr)$_4$ and the NaBH$_4$ in the second step. Further, the use of monosubstituted diamines, such as commercially available N-phenylethylenediamine, in the second step has the potential to eliminate the need for palladium catalyzed coupling reactions. Additionally, the methodology may prove amenable to scale-up.

The various catalyst systems and components that may be used to generate the polymers and molecular weight compositions disclosed are discussed in the sections to follow. The first section discusses catalyst compounds that can be used in embodiments, including non-metallocene catalysts, among others. The second section discusses the physical forms of the catalyst that may be used, such as a dry catalyst powder or a catalyst slurry. The third section discusses supports that may be used. The fourth section discusses activators that may be used. The fifth section discusses continuity additives or static control agents that may be used in gas phase polymerizations. The sixth section discusses polymerization processes that may be used with the current catalysts, including parameters that may be measured and used to control the process. Exemplary techniques for forming the compounds described in embodiments herein are shown in the examples section that follows.

Catalyst Compounds

Group 15 Atom and Non-metallocene Catalyst Compounds

The catalyst system can include one or more Group 15 metal-containing catalyst compounds, such as shown in structure (I), above. As used herein, these are termed non-metallocene catalyst compounds. The Group 15 metal-containing compound generally includes a Group 3 to 14 metal atom, a Group 3 to 7, or a Group 4 to 6 metal atom. In many embodiments, the Group 15 metal-containing compound includes a Group 4 metal atom bound to at least one leaving group and also bound to at least two Group 15 atoms, at least one of which is also bound to a Group 15 or 16 atom through another group.

In one or more embodiments, at least one of the Group 15 atoms is also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and can optionally be bound to hydrogen, a halogen, a heteroatom or a hydrocarbyl group, or a heteroatom containing group.

The Group 15-containing metal compounds can be described more particularly with respect to structures (IV) or (V).

(IV)

(V)

In structures (IV) and (V), M is a Group 3 to 12 transition metal or a Group 13 or 14 main group metal, a Group 4, 5, or 6 metal. In many embodiments, M is a Group 4 metal, such as zirconium, titanium, or hafnium. Each X is independently a leaving group, such as an anionic leaving group. The leaving group may include a hydrogen, a hydrocarbyl group, a benzyl, a heteroatom, a halogen, or an alkyl; y is 0 or 1 (when y is 0 group L' is absent). The term 'n' is the oxidation state of M. In various embodiments, n is +3, +4, or +5. In many embodiments, n is +4. The term 'm' represents the formal charge of the YZL or the YZL' ligand, and is 0, −1, −2 or −3 in various embodiments. In many embodiments, m is −2. L is a Group 15 or 16 element, such as nitrogen or oxygen; L' is a Group 15 or 16 element or Group 14 containing group, such as carbon, silicon or germanium. Y is a Group 15 element, such as nitrogen or phosphorus. In many embodiments, Y is nitrogen. Z is a Group 15 element, such as nitrogen or phosphorus. In many embodiments, Z is nitrogen. $R^1$ and $R^2$ are, independently, a $C_1$ to $C_{20}$ hydrocarbon group, a heteroatom containing group having up to twenty carbon atoms, silicon, germanium, tin, lead, or phosphorus. In many embodiments, $R^1$ and $R^2$ are a $C_2$ to $C_{20}$ alkyl, aryl or aralkyl group, such as a linear, branched or cyclic $C_2$ to $C_{20}$ alkyl group, or a $C_2$ to $C_6$ hydrocarbon group, such as the X described with respect to structures (VI) and (VII) above. $R^1$ and $R^2$ may also be interconnected to each other. In some embodiments, $R^1$ and $R^2$ may be further substituted, for example, if either $R^1$ or $R^2$ is an ethyl group, an aryl group, an alkyl group, or other substituents, may be located along the chain. For example, an aryl group may be located on the carbon atom nearest L. $R^3$ may be absent or may be a hydrocarbon group, a hydrogen, a halogen, a heteroatom containing group.

In many embodiments, $R^3$ is absent, for example, if L is an oxygen, or a hydrogen, or a linear, cyclic, or branched alkyl group having 1 to 20 carbon atoms. $R^4$ and $R^5$ are independently an alkyl group, an aryl group, substituted aryl group, a cyclic alkyl group, a substituted cyclic alkyl group, a cyclic aralkyl group, a substituted cyclic aralkyl group, or multiple ring system, often having up to 20 carbon atoms. In many embodiments, $R^4$ and $R^5$ have between 3 and 10 carbon atoms, or are a $C_1$ to $C_{20}$ hydrocarbon group, a $C_1$ to $C_{20}$ aryl group or a $C_1$ to $C_{20}$ aralkyl group, or a heteroatom containing group. $R^4$ and $R^5$ may be interconnected to each other. $R^6$ and $R^7$ are independently absent, hydrogen, an alkyl group, halogen, heteroatom, or a hydrocarbyl group, such as a linear, cyclic or branched alkyl group having 1 to 20 carbon atoms. In many embodiments, $R^6$ and $R^7$ are absent. $R^*$ may be absent, or may be a hydrogen, a Group 14 atom containing group, a halogen, or a heteroatom containing group.

By "formal charge of the YZL or YZL' ligand," it is meant the charge of the entire ligand absent the metal and the leaving groups X. By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups. An alkyl group may be linear, branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In one or more embodiments, $R^4$ and $R^5$ are independently a group represented by the structure (VI).

Bond to Z or Y

When $R^4$ and $R^5$ are as in structure (VI), $R^8$ to $R^{12}$ are each independently hydrogen, a $C_1$ to $C_{40}$ alkyl group, a halide, a heteroatom, a heteroatom containing group containing up to 40 carbon atoms. In many embodiments, $R^8$ to $R^{12}$ are a $C_1$ to $C_{20}$ linear or branched alkyl group, such as a methyl, ethyl, propyl, or butyl group. Any two of the R groups may form a cyclic group and/or a heterocyclic group. The cyclic groups may be aromatic. In one embodiment $R^9$, $R^{10}$ and $R^{12}$ are independently a methyl, ethyl, propyl, or butyl group (including all isomers). In another embodiment, $R^9$, $R^{10}$ and $R^{12}$ are methyl groups, and $R^8$ and $R^{11}$ are hydrogen.

In one or more embodiments, $R^4$ and $R^5$ are both a group represented by structure (VII).

Bond to Z or Y

When $R^4$ and $R^5$ follow structure (VII), M is a Group 4 metal, such as zirconium, titanium, or hafnium. In many embodiments, M is zirconium. Each of L, Y, and Z may be a nitrogen. Each of $R^1$ and $R^2$ may be —CH$_2$—CH$_2$—. $R^3$ may be hydrogen, and $R^6$ and $R^7$ may be absent.

Representative Group 15-containing metal compounds and preparation thereof can be as discussed and described in U.S. Pat. Nos. 5,318,935; 5,889,128; 6,333,389; 6,271,325; and 6,689,847; WO Publications WO 99/01460; WO 98/46651; WO 2009/064404; WO 2009/064452; and WO 2009/064482; and EP 0 893 454; and EP 0 894 005.

In some embodiments, the Group 15 metal-containing catalyst compound may have structure (VIII).

In structure (VIII), M may be a group 4 element, such as Ti, Zr, or Hf. R may be an aryl group, a substituted aryl group, or an alkyl group comprising 2 to 20 carbons. Ar may be an aryl group or a substituted aryl group, and Ar' may be an aryl group or a substituted aryl group. Each X may individually be a hydride, a methyl group, an alkyl group, a benzyl group, an amide group, or a halo group, such as a chloro group, a bromo group, a fluoro group, or an iodo group.

An example of a group 15 metal containing catalyst compound that may be formed in embodiments described herein is shown in structure (IX).

Metallocene Catalyst Compounds

Metallocene catalyst compounds are generally described 1 & 2 METALLOCENE-BASED POLYOLEFINS (John Scheirs & W. Kaminsky eds., John Wiley & Sons, Ltd. 2000); G. G. Hlatky in 181 COORDINATION CHEM. REV. 243-296 (1999); and, in particular, for use in the synthesis of polyethylene in 1 METALLOCENE-BASED POLYOLEFINS 261-377 (2000). The metallocene catalyst compounds can include "half sandwich" and/or "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The Cp ligands are one or more rings or ring system(s), at least a portion of which includes π-bonded systems, such as cycloalkadienyl ligands and heterocyclic analogues. The ring(s) or ring system(s) typically include atoms selected from the group consisting of Groups 13 to 16 atoms, and, in a particular exemplary embodiment, the atoms that make up the Cp ligands are selected from the group consisting of carbon, nitrogen, oxygen, silicon, sulfur, phosphorous, germanium, boron, aluminum, and combinations thereof, where carbon makes up at least 50% of the ring members. In a more particular exemplary embodiment, the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "H$_4$ Ind"), substituted versions thereof (as discussed and described in more detail below), and heterocyclic versions thereof.

The metal atom "M" of the metallocene catalyst compound can be selected from the group consisting of Groups 3 through 12 atoms and lanthanide Group atoms in one exemplary embodiment; and selected from the group consisting of Groups 3 through 10 atoms in a more particular exemplary embodiment; and selected from the group consisting of Sc, Ti, Zr, Hf, V, Nb, Ta, Mn, Re, Fe, Ru, Os, Co, Rh, Ir, and Ni in yet a more particular exemplary embodiment; and selected from the group consisting of Groups 4, 5, and 6 atoms in yet a more particular exemplary embodiment; and Ti, Zr, Hf atoms in yet a more particular exemplary embodiment; and Zr in yet a more particular exemplary embodiment. The oxidation state of the metal atom "M" can range from 0 to +7 in one exemplary embodiment; and in a more particular exemplary embodiment, can be +1, +2, +3, +4, or +5; and in yet a more particular exemplary embodiment can be +2, +3 or +4. The groups bound to the metal atom "M" are such that the compounds described below in the formulas and structures are electrically neutral, unless otherwise indicated. The Cp ligand forms at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst compounds can be represented by structure (X).

$$Cp^A Cp^B MX_n \qquad (X)$$

In structure (X), M is as described above; each X is chemically bonded to M; each Cp group is chemically bonded to M; and n is 0 or an integer from 1 to 4, and either 1 or 2 in a particular exemplary embodiment.

The ligands represented by $Cp^A$ and $Cp^B$ in structure (X) can be the same or different cyclopentadienyl ligands or ligands isolobal to cyclopentadienyl, either or both of which can contain heteroatoms and either or both of which can be substituted by a group R. In at least one specific embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of structure (X) can be unsubstituted or substituted with any one or combination of substituent groups R. Non-limiting examples of substituent groups R as used in structure (X) as well as ring substituents in structures discussed and described below, include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. More particular non-limiting examples of alkyl substituents R associated with structures (X) through (XV) include methyl, ethyl, propyl, butyl, pentyl, hexyl, cyclopentyl, cyclohexyl, benzyl, phenyl, methylphenyl, and tert-butylphenyl groups and the like, including all their isomers, for example, tertiary-butyl, isopropyl, and the like. Other possible radicals include substituted alkyls and aryls such as, for example, fluoromethyl, fluroethyl, difluroethyl, iodopropyl, bromohexyl, chlorobenzyl, hydrocarbyl substituted organometalloid radicals including trimethylsilyl, trimethylgermyl, methyldiethylsilyl, and the like, and halocarbyl-substituted organometalloid radicals, including tris(trifluoromethyl)silyl, methylbis(difluoromethyl)silyl, bromomethyldimethylgermyl and the like; and disubstituted boron radicals including dimethylboron, for example; and disubstituted Group 15 radicals including dimethylamine, dimethylphosphine, diphenylamine, methylphenylphosphine, as well as Group 16 radicals including methoxy, ethoxy, propoxy, phenoxy, methylsulfide and ethylsulfide. Other substituent groups R include, but are not limited to, olefins such as olefinically unsaturated substituents including vinyl-terminated ligands such as, for example, 3-butenyl, 2-propenyl, 5-hexenyl, and the like. In one exemplary embodiment, at least two R groups (two adjacent R groups in a particular exemplary embodiment) are joined to form a ring structure having from 3 to 30 atoms selected from the group consisting of carbon, nitrogen, oxygen, phosphorous, silicon, germanium, aluminum, boron, and combinations thereof. Also, a substituent group R such as 1-butanyl can form a bonding association to the element M.

Each leaving group, or X, in the structure (X) above and for the structures in (XI) through (XIII) below is independently selected from the group consisting of: halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_8$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof, in a more particular exemplary embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular exemplary embodiment; hydride, chloride, fluoride, methyl, phenyl, phenoxy, benzoxy, tosyl, fluoromethyls and fluorophenyls, in yet a more particular exemplary embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls, and $C_1$ to $C_{12}$ heteroatom-containing alkylaryls, in yet a more particular exemplary embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls, in yet a more particular exemplary embodiment; chloride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls), in yet a more particular exemplary embodiment.

Other non-limiting examples of X groups include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides, halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one exemplary embodiment, two or more X's form a part of a fused ring or ring system. In at least one specific embodiment, X can be a leaving group selected from the group consisting of chloride ions, bromide ions, $C_1$ to $C_{10}$ alkyls, and $C_2$ to $C_{12}$ alkenyls, carboxylates, acetylacetonates, and alkoxides.

The metallocene catalyst compound includes those of structure (X) where $Cp^A$ and $Cp^B$ are bridged to each other by at least one bridging group, (A), such that the structure is represented by structure (XI).

$$Cp^A(A)Cp^B MX_n \qquad (XI)$$

The bridged compounds represented by structure (XI) are known as "bridged metallocenes." The elements $Cp^A$, $Cp^B$, M, X and n in structure (XI) are as defined above for structure (X); where each Cp ligand is chemically bonded to M, and (A) is chemically bonded to each Cp. The bridging group (A) can include divalent hydrocarbon groups containing at least one Group 13 to 16 atom, such as, but not limited to, at least one of a carbon, oxygen, nitrogen, silicon, aluminum, boron, germanium, tin atom, and combinations thereof; where the heteroatom can also be $C_1$ to $C_{12}$ alkyl or aryl substituted to satisfy neutral valency. In at least one specific embodiment, the bridging group (A) can also include substituent groups R as defined above (for structure (X)) including halogen radicals and iron. In at least one specific embodiment, the bridging group (A) can be represented by $C_1$ to $C_6$ alkylenes, substituted $C_1$ to $C_6$ alkylenes, oxygen, sulfur, $R'_2C=$, $R'_2Si=$, $=Si(R')_2Si(R'_2)=$, $R'_2Ge=$, and $R'P=$, where "=" represents two chemical bonds, R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and where two or more R' can be joined to form a ring or ring system. In at least one specific embodiment, the bridged metallocene catalyst compound of structure (XI) includes two or more bridging groups (A). In one or more embodiments, (A) can be a divalent bridging group bound to both $Cp^A$ and $Cp^B$ selected from the group consisting of divalent $C_1$ to $C_{20}$ hydrocarbyls and $C_1$ to $C_{20}$ heteroatom containing hydrocarbonyls, where the heteroatom containing hydrocarbonyls include from one to three heteroatoms.

The bridging group (A) can include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties where the Si atom is replaced by a Ge or a C atom; as well as dimethylsilyl, diethylsilyl, dimethylgermyl and diethylgermyl.

The bridging group (A) can also be cyclic, having, for example, 4 to 10 ring members; in a more particular exemplary embodiment, bridging group (A) can have 5 to 7 ring members. The ring members can be selected from the elements mentioned above, and, in a particular embodiment, can be selected from one or more of B, C, Si, Ge, N, and O. Non-limiting examples of ring structures which can be present as, or as part of, the bridging moiety are cyclobutylidene, cyclopentylidene, cyclohexylidene, cycloheptylidene, cyclooctylidene and the corresponding rings where one or two carbon atoms are replaced by at least one of Si, Ge, N and O. In one or more embodiments, one or two carbon atoms can be replaced by at least one of Si and Ge. The bonding arrangement between the ring and the Cp groups can be cis-, trans-, or a combination thereof.

The cyclic bridging groups (A) can be saturated or unsaturated and/or can carry one or more substituents and/or can be fused to one or more other ring structures. If present, the one or more substituents can be, in at least one specific embodiment, selected from the group consisting of hydrocarbyl (e.g., alkyl, such as methyl) and halogen (e.g., F, Cl). The one or more Cp groups to which the above cyclic bridging moieties can optionally be fused can be saturated or unsaturated, and are selected from the group consisting of those having 4 to 10, more particularly 5, 6, or 7 ring members (selected from the group consisting of C, N, O, and S in a particular exemplary embodiment) such as, for example, cyclopentyl, cyclohexyl and phenyl. Moreover, these ring structures can themselves be fused such as, for example, in the case of a naphthyl group. Moreover, these (optionally fused) ring structures can carry one or more substituents. Illustrative, non-limiting examples of these substituents are hydrocarbyl (particularly alkyl) groups and halogen atoms. The ligands $Cp^A$ and $Cp^B$ of structures (X) and (XI) can be different from each other. The ligands $Cp^A$ and $Cp^B$ of structures (X) and (XI) can be the same.

The metallocene catalyst compound can include bridged mono-ligand metallocene compounds (e.g., mono cyclopentadienyl catalyst components). Exemplary metallocene catalyst compounds are further described in U.S. Pat. No. 6,943,134.

It is contemplated that the metallocene catalyst components discussed and described above include their structural or optical or enantiomeric isomers (racemic mixture), and, in one exemplary embodiment, can be a pure enantiomer. As used herein, a single, bridged, asymmetrically substituted metallocene catalyst compound having a racemic and/or meso isomer does not, itself, constitute at least two different bridged, metallocene catalyst components.

The amount of the transition metal component of the one or more metallocene catalyst compounds in the catalyst system can range from a low of about 0.2 wt. %, about 3 wt. %, about 0.5 wt. %, or about 0.7 wt. % to a high of about 1 wt. %, about 2 wt. %, about 2.5 wt. %, about 3 wt. %, about 3.5 wt. %, or about 4 wt. %, based on the total weight of the catalyst system.

The metallocene catalyst compounds can include any combination of any embodiment discussed and described herein. For example, the metallocene catalyst compound can include, but is not limited to, bis(n-butylcyclopentadienyl) zirconium $(CH_3)_2$, bis(n-butylcyclopentadienyl) zirconium $Cl_2$, bis(n-butylcyclopentadienyl) zirconium $Cl_2$, (n-propylcyclopentadienyl, tetramethylcyclopentadienyl) zirconium $Cl_2$, or any combinations thereof.

In addition to the metallocene catalyst compounds discussed and described above, other suitable metallocene catalyst compounds can include, but are not limited to, metallocenes discussed and described in U.S. Pat. Nos. 7,741,417; 7,179,876; 7,169,864; 7,157,531; 7,129,302; 6,995,109; 6,958,306; 6,884,748; 6,689,847; and WO Publications: WO 1997/022635; WO 1998/046651; WO 2000/069922; WO 2001/030860; WO 2001/030861; WO 2002/046246; WO 2002/050088; WO 2004/026921; and WO 06/019494.

Although the catalyst compounds may be written or shown with methyl-, chloro-, or benzyl-leaving groups attached to the central metal, it can be understood that these groups may be different without changing the catalyst involved. For example, each of these ligands may independently be a Benzyl group (Bn), a methyl group (Me), a chloro group (Cl), a fluoro group (F), or any number of other groups, including organic groups, or heteroatom groups.

Further, these ligands will change during the reaction, as a pre-catalyst is converted to the active catalyst for the reaction.

Catalyst Forms

Any number of combinations of catalyst components may be used in embodiments. For example, the catalyst mentioned above may be used alone or in combinations with other catalysts, such as metallocenes. The catalysts can be formed together to make a dry catalyst powder that is directly added to the reactor, or may be used in a slurry formed from the catalyst, an activator, and a support.

A catalyst slurry may be used in a catalyst trim system wherein a second catalyst is added to the slurry to broaden the molecular weight distribution of the resulting polymer. The slurry may include one or more activators and supports, and one more catalyst compounds. For example, the slurry may include two or more activators (such as alumoxane and a modified alumoxane) and a catalyst compound, or the slurry may include a supported activator and more than one catalyst compounds. In one embodiment, the slurry includes a support, an activator, and two catalyst compounds. In another embodiment the slurry includes a support, an activator and two different catalyst compounds, which may be added to the slurry separately or in combination. The slurry, containing silica and alumoxane, may be contacted with a catalyst compound, allowed to react, and thereafter the slurry is contacted with another catalyst compound, for example, in a trim system.

The molar ratio of metal in the activator to metal in the catalyst compound in the slurry may be 1000:1 to 0.5:1, 300:1 to 1:1, or 150:1 to 1:1. The slurry can include a support material which may be any inert particulate carrier material known in the art, including, but not limited to, silica, fumed silica, alumina, clay, talc or other support materials such as disclosed above. In one embodiment, the slurry contains silica and an activator, such as methyl aluminoxane ("MAO"), modified methyl aluminoxane ("MMAO"), as discussed further below.

One or more diluents or carriers can be used to facilitate the combination of any two or more components of the catalyst system in the slurry or in the trim catalyst solution. For example, the single site catalyst compound and the activator can be combined together in the presence of toluene or another non-reactive hydrocarbon or hydrocarbon mixture to provide the catalyst mixture. In addition to toluene, other suitable diluents can include, but are not limited to, ethylbenzene, xylene, pentane, hexane, heptane, octane, other hydrocarbons, or any combination thereof. The support, either dry or mixed with toluene can then be added to the catalyst mixture or the catalyst/activator mixture can be added to the support.

The catalyst is not limited to a slurry arrangement, as a mixed catalyst system may be made on a support and dried. The dried catalyst system can then be fed to the reactor through a dry feed system.

Support

As used herein, the terms "support" and "carrier" are used interchangeably and refer to any support material, including a porous support material, such as talc, inorganic oxides, and inorganic chlorides. The one or more catalyst compounds can be supported on the same or separate supports together with the activator, or the activator can be used in an unsupported form, or can be deposited on a support different from the single site catalyst compounds, or any combination thereof. This may be accomplished by any technique commonly used in the art. There are various other methods in the art for supporting a catalyst compound. For example, the catalyst compound can contain a polymer bound ligand as described in, for example, U.S. Pat. Nos. 5,473,202 and 5,770,755. The catalyst compounds of the slurry can be spray dried as described in, for example, U.S. Pat. No. 5,648,310. The support used with the catalyst compound can be functionalized, as described in EP 0 802 203, or at least one substituent or leaving group is selected as described in U.S. Pat. No. 5,688,880.

The support can be or include one or more inorganic oxides, for example, of Group 2, 3, 4, 5, 13, or 14 elements. The inorganic oxide can include, but is not limited to silica, alumina, titania, zirconia, boria, zinc oxide, magnesia, or any combination thereof. Illustrative combinations of inorganic oxides can include, but are not limited to, alumina-silica, silica-titania, alumina-silica-titania, alumina-zirconia, alumina-titania, and the like. The support can be or include silica, alumina, or a combination thereof. In one embodiment described herein, the support is silica.

Suitable commercially available silica supports can include, but are not limited to, ES757, ES70, and ES70W available from PQ Corporation. Suitable commercially available silica-alumina supports can include, but are not limited to, SIRAL® 1, SIRAL® 5, SIRAL® 10, SIRAL® 20, SIRAL® 28M, SIRAL® 30, and SIRAL® 40, available from SASOL®. Catalyst supports comprising silica gels with activators, such as methylaluminoxanes (MAOs), can be used in trim systems, since these supports may function better for cosupporting solution carried catalysts.

Suitable catalyst supports are discussed and described in Hlatky, Chem. Rev. (2000), 100, 1347 1376 and Fink et al., Chem. Rev. (2000), 100, 1377 1390, U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664, and WO 95/32995, WO 95/14044, WO 96/06187, and WO 97/02297.

Activator

As used herein, the term "activator" may refer to any compound or combination of compounds, supported, or unsupported, which can activate a catalyst compound or component, such as by creating a cationic species of the catalyst component. For example, this can include the abstraction of at least one leaving group (the "X" group in the single site catalyst compounds described herein) from the metal center of the single site catalyst compound/component. The activator may also be referred to as a "co-catalyst".

For example, the activator can include a Lewis acid or a non-coordinating ionic activator or ionizing activator, or any other compound including Lewis bases, aluminum alkyls, and/or conventional-type co-catalysts. Illustrative activators can include, but are not limited to, methylaluminoxane ("MAO") and modified methylaluminoxane ("MMAO"), and/or ionizing compounds, neutral or ionic, such as tri (n-butyl)ammonium tetrakis(pentafluorophenyl)boron, dimethylanilinium tetrakis(pentafluorophenyl) boron a trisperfluorophenyl boron metalloid precursor, a trisperfluoronaphthyl boron metalloid precursor, or any combinations thereof. Further, activators may include titanium halides, titanium alkoxides, and organo-titanium compounds, such as titanium (IV) chloride, titanium (IV) tetra(isopropoxide), tetraethyl titanate, or any number of other suitable titanium compounds.

Aluminoxanes can be described as oligomeric aluminum compounds having —Al(R)—O— subunits, where R is an alkyl group. Examples of aluminoxanes include, but are not limited to, methylaluminoxane ("MAO"), modified methylaluminoxane ("MMAO"), ethylaluminoxane, isobutylaluminoxane, or a combination thereof. Aluminoxanes can be produced by the hydrolysis of the respective trialkylaluminum compound. MMAO can be produced by the hydrolysis of trimethylaluminum and a higher trialkylaluminum, such as triisobutylaluminum. MMAOs are generally more soluble in aliphatic solvents and more stable during storage. There are a variety of methods for preparing aluminoxane and modified aluminoxanes, non-limiting examples can be as discussed and described in U.S. Pat. Nos. 4,665,208; 4,952,540; 5,091,352; 5,206,199; 5,204,419; 4,874,734; 4,924,018; 4,908,463; 4,968,827; 5,308,815; 5,329,032; 5,248,801; 5,235,081; 5,157,137; 5,103,031; 5,391,793; 5,391,529; 5,693,838; 5,731,253; 5,731,451; 5,744,656; 5,847,177; 5,854,166; 5,856,256; and 5,939,346; and EP 0 561 476; EP 0 279 586; EP 0 594-218; and EP 0 586 665; and WO Publications WO 94/10180 and WO 99/15534.

As noted above, one or more organo-aluminum compounds such as one or more alkylaluminum compounds can be used in conjunction with the aluminoxanes. For example, alkylaluminum species that may be used are diethylaluminum ethoxide, diethylaluminum chloride, and/or diisobutylaluminum hydride. Examples of trialkylaluminum compounds include, but are not limited to, trimethylaluminum, triethylaluminum ("TEAL"), triisobutylaluminum ("TiBAl"), tri-n-hexylaluminum, tri-n-octylaluminum, tripropylaluminum, tributylaluminum, and the like.

Continuity Additive/Static Control Agent

In gas-phase polyethylene production processes, it may be desirable to use one or more static control agents to aid in regulating static levels in the reactor. As used herein, a static control agent is a chemical composition which, when introduced into a fluidized bed reactor, may influence or drive the static charge (negatively, positively, or to zero) in the fluidized bed. The specific static control agent used may depend upon the nature of the static charge, and the choice of static control agent may vary dependent upon the polymer being produced and the single site catalyst compounds being used. For example, the use of static control agents is disclosed in European Patent No. 0229368 and U.S. Pat. Nos. 4,803,251; 4,555,370; and 5,283,278, and references cited therein.

Control agents such as aluminum stearate may be employed. The static control agent used may be selected for its ability to receive the static charge in the fluidized bed without adversely affecting productivity. Other suitable static control agents may also include aluminum distearate, ethoxlated amines, and anti-static compositions such as those provided by Innospec Inc. under the trade name OCTASTAT. For example, OCTASTAT 2000 is a mixture of a polysulfone copolymer, a polymeric polyamine, and oil-soluble sulfonic acid.

Any of the aforementioned control agents, as well as those described in, for example, WO 2001/044322, listed under the heading Carboxylate Metal Salt and including those chemicals and compositions listed as antistatic agents may be employed either alone or in combination as a control agent. For example, the carboxylate metal salt may be combined with an amine containing control agent (e.g., a carboxylate metal salt with any family member belonging to the KEMAMINE® (available from Crompton Corporation) or ATMER® (available from ICI Americas Inc.) family of products).

Other useful continuity additives include ethyleneimine additives useful in embodiments disclosed herein may include polyethyleneimines having the following general formula:

in which n may be from about 10 to about 10,000. The polyethyleneimines may be linear, branched, or hyperbranched (e.g., forming dendritic or arborescent polymer structures). They can be a homopolymer or copolymer of ethyleneimine or mixtures thereof (referred to as polyethyleneimine(s) hereafter). Although linear polymers represented by the chemical formula —[CH$_2$—CH$_2$—NH]— may be used as the polyethyleneimine, materials having primary, secondary, and tertiary branches can also be used. Commercial polyethyleneimine can be a compound having branches of the ethyleneimine polymer.

Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF.

Another useful continuity additive can include a mixture of aluminum distearate and an ethoxylated amine-type compound, e.g., IRGASTAT AS-990, available from Huntsman (formerly Ciba Specialty Chemicals). The mixture of aluminum distearate and ethoxylated amine type compound can be slurried in mineral oil e.g., Hydrobrite 380. For example, the mixture of aluminum distearate and an ethoxylated amine type compound can be slurried in mineral oil to have total slurry concentration of ranging from about 5 wt. % to about 50 wt. % or about 10 wt. % to about 40 wt. %, or about 15 wt. % to about 30 wt. %. Other useful static control agents and additives are disclosed in U.S. Patent Application Publication No. 2008/0045663.

The continuity additive(s) or static control agent(s) may be added to the reactor in an amount ranging from 0.05 to 200 ppm, based on the weight of all feeds to the reactor, excluding recycle. In some embodiments, the continuity additive may be added in an amount ranging from 2 to 100 ppm, or in an amount ranging from 4 to 50 ppm.

Polymerization Process

The catalyst system can be used to polymerize one or more olefins, such as ethylene, to provide one or more polymer products therefrom. Any suitable polymerization process can be used, including, but not limited to, high pressure, solution, slurry, and/or gas phase polymerization processes.

As used herein, the terms "polyethylene" and "polyethylene copolymer" refer to a polymer having at least 50 wt. % ethylene-derived units. In various embodiments, the polyethylene can have at least 70 wt. % ethylene-derived units, at least 80 wt. % ethylene-derived units, at least 90 wt. % ethylene-derived units, or at least 95 wt. % ethylene-derived units. The polyethylene polymers described herein are generally copolymer, but may also include terpolymers, having one or more other monomeric units. As described herein, a polyethylene can include, for example, at least one or more other olefins or comonomers. Suitable comonomers can contain 3 to 16 carbon atoms, from 3 to 12 carbon atoms, from 4 to 10 carbon atoms, and from 4 to 8 carbon atoms. Examples of comonomers include, but are not limited to, propylene, 1-butene, 1-pentene, 1-hexene, 1-heptene, 1-octene, 4-methylpent-1-ene, 1-decene, 1-dodecene, 1-hexadecene, and the like.

A gas phase polymerization may be conducted in a fluidized bed reactor which can include a reaction zone and a velocity reduction zone. The reaction zone can include a bed that includes growing polymer particles, formed polymer particles and a minor amount of catalyst particles fluidized by the continuous flow of the gaseous monomer and diluent to remove heat of polymerization through the reaction zone. Optionally, some of the re-circulated gases can be cooled and compressed to form liquids that increase the heat removal capacity of the circulating gas stream when readmitted to the reaction zone. A suitable rate of gas flow can be readily determined by experimentation. Make-up of gaseous monomer to the circulating gas stream can be at a rate equal to the rate at which particulate polymer product and monomer associated therewith is withdrawn from the reactor and the composition of the gas passing through the reactor can be adjusted to maintain an essentially steady state gaseous composition within the reaction zone. The gas leaving the reaction zone can be passed to the velocity reduction zone where entrained particles are removed, for example, by slowing and falling back to the reaction zone. If desired, finer entrained particles and dust can be removed in a separation system, such as a cyclone and/or fines filter. The gas can be passed through a heat exchanger where at least a portion of the heat of polymerization can be removed. The gas can then be compressed in a compressor and returned to the reaction zone. Additional reactor details and means for operating the reactor are described in, for example, U.S. Pat. Nos. 3,709,853; 4,003,712; 4,011,382; 4,302,566; 4,543,399; 4,882,400; 5,352,749; and 5,541,270; EP 0802202; and Belgian Patent No. 839,380.

The reactor temperature of the fluid bed process can be greater than about 30° C., about 40° C., about 50° C., about 90° C., about 100° C., about 110° C., about 120° C., about 150° C., or higher. In general, the reactor temperature is operated at the highest feasible temperature taking into account the sintering temperature of the polymer product within the reactor. Thus, the upper temperature limit in one embodiment is the melting temperature of the polyethylene copolymer produced in the reactor. However, higher temperatures may result in narrower MWDs, which can be improved by the addition of structure (IV), or other co-catalysts, as described herein.

Hydrogen gas can be used in olefin polymerization to control the final properties of the polyolefin, such as described in the "Polypropylene Handbook," at pages 76-78 (Hanser Publishers, 1996). Using certain catalyst systems, increasing concentrations (partial pressures) of hydrogen can increase the flow index (FI), or melt index (MI) of the polyethylene copolymer generated. The flow index can thus be influenced by the hydrogen concentration. The amount of hydrogen in the polymerization can be expressed as a mole ratio relative to the total polymerizable monomer, for example, ethylene, or a blend of ethylene and hexene or propylene.

The amount of hydrogen used in the polymerization process can be an amount necessary to achieve the desired flow index of the final polyolefin polymer. For example, the mole ratio of hydrogen to total monomer ($H_2$:monomer) can be greater than about 0.0001, greater than about 0.0005, or greater than about 0.001. Further, the mole ratio of hydrogen to total monomer ($H_2$:monomer) can be less than about 10, less than about 5, less than about 3, and less than about 0.10. A desirable range for the mole ratio of hydrogen to monomer can include any combination of any upper mole ratio limit with any lower mole ratio limit described herein. Expressed another way, the amount of hydrogen in the reactor at any time can range to up to about 5,000 ppm, up to about 4,000 ppm in another embodiment, up to about 3,000 ppm, or between about 50 ppm and 5,000 ppm, or between about 50 ppm and 2,000 ppm in another embodiment. The amount of hydrogen in the reactor can range from a low of about 1 ppm, about 50 ppm, or about 100 ppm to a high of about 400 ppm, about 800 ppm, about 1,000 ppm, about 1,500 ppm, or about 2,000 ppm, based on weight. Further, the ratio of hydrogen to total monomer ($H_2$:monomer) can be about 0.00001:1 to about 2:1, about 0.005:1 to about 1.5:1, or about 0.0001:1 to about 1:1. The one or more reactor pressures in a gas phase process (either single stage or two or more stages) can vary from 690 kPa (100 psig) to 3,448 kPa (500 psig), in the range from 1,379 kPa (200 psig) to 2,759 kPa (400 psig), or in the range from 1,724 kPa (250 psig) to 2,414 kPa (350 psig).

The gas phase reactor can be capable of producing from about 10 kg of polymer per hour (25 lbs/hr) to about 90,900 kg/hr (200,000 lbs/hr), or greater, and greater than about 455 kg/hr (1,000 lbs/hr), greater than about 4,540 kg/hr (10,000 lbs/hr), greater than about 11,300 kg/hr (25,000 lbs/hr), greater than about 15,900 kg/hr (35,000 lbs/hr), and greater than about 22,700 kg/hr (50,000 lbs/hr), and from about 29,000 kg/hr (65,000 lbs/hr) to about 45,500 kg/hr (100,000 lbs/hr).

A slurry polymerization process may be used to prepare polymer in embodiments. A slurry polymerization process generally uses pressures in the range of from about 101 kPa (1 atmosphere) to about 5,070 kPa (50 atmospheres) or greater, and temperatures in the range of from about 0° C. to about 120° C., and more particularly from about 30° C. to about 100° C. In a slurry polymerization, a suspension of solid, particulate polymer can be formed in a liquid polymerization diluent medium to which ethylene, comonomers, and hydrogen along with catalyst can be added. The suspension including diluent can be intermittently or continuously removed from the reactor where the volatile components are separated from the polymer and recycled, optionally after a distillation, to the reactor. The liquid diluent employed in the polymerization medium can be an alkane having from 3 to 7 carbon atoms, such as, for example, a branched alkane. The medium employed should be liquid under the conditions of polymerization and relatively inert. When a propane medium is used the process should be operated above the reaction diluent critical temperature and pressure. A hexane, isopentane, or isobutane medium can be employed. The slurry can be circulated in a continuous loop system.

The product polyethylene can have a melt index ratio (MIR or $I_{21}/I_2$) ranging from about 10 to less than about 300, or, in many embodiments, from about 15 to about 150. Flow index (FI, HLMI, or $I_{21}$ can be measured in accordance with ASTM D1238 (190° C., 21.6 kg). The melt index (MI, $I_2$) can be measured in accordance with ASTM D1238 (at 190° C., 2.16 kg weight).

Density can be determined in accordance with ASTM D-792. Density is expressed as grams per cubic centimeter (g/cm$^3$) unless otherwise noted. The polyethylene can have a density ranging from a low of about 0.89 g/cm$^3$, about 0.90 g/cm$^3$, or about 0.91 g/cm$^3$ to a high of about 0.95 g/cm$^3$, about 0.96 g/cm$^3$, or about 0.97 g/cm$^3$. The polyethylene can have a bulk density, measured in accordance with ASTM D1895 method B, of from about 0.25 g/cm$^3$ to about 0.5 g/cm$^3$. For example, the bulk density of the polyethylene can range from a low of about 0.30 g/cm$^3$, about 0.32 g/cm$^3$, or about 0.33 g/cm$^3$ to a high of about 0.40 g/cm$^3$, about 0.44 g/cm$^3$, or about 0.48 g/cm$^3$.

The polyethylene can be suitable for such articles as films, fibers, nonwoven and/or woven fabrics, extruded articles, and/or molded articles. Examples of films include blown or cast films formed in single layer extrusion, coextrusion, or lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Examples of fibers include melt spinning, solution spinning and melt blown fiber operations for use in woven or non-woven form to make filters, diaper fabrics, hygiene products, medical garments, geotextiles, etc. Examples of extruded articles include tubing, medical tubing, wire and cable coatings, pipe, geomembranes, and pond liners. Examples of molded articles include single and multi-layered constructions by injection molding or rotation molding or blow molding processes in the form of bottles, tanks, large hollow articles, rigid food containers and toys, etc.

EXAMPLES

General: All reactions were carried out under a purified nitrogen atmosphere using standard glovebox, high vacuum or Schlenk techniques, unless otherwise noted. All solvents used were anhydrous, sparged with nitrogen and stored over 4 Å molecular sieves. All starting materials were either purchased from Aldrich and purified prior to use or prepared according to procedures known to those skilled in the art. Josiphos was purchased from Strem and used as received. Benzene-$d_6$ was purchased from Cambridge Isotope Labs, sparged with nitrogen, and stored over 4 Å molecular sieves. $^1$H NMR spectroscopy on ligand and catalyst samples was performed on a Bruker Avance III 400 MHz instrument.

Representative Synthetic Examples

Ligands

Step 1 of the ligand synthesis was performed using scheme (3).

Preparation of 1-phenyl-2-(phenylamino)ethanone

A 1-liter round bottom flask was charged with ethanol (500 mL), 2-bromoacetophenone (40 g, 0.20 mol), aniline (20 mL, 0.22 mol), and sodium carbonate (80 g, 0.76 mol) under ambient air. The contents were agitated with a mechanical stirrer while the flask was heated to 70° C. in an oil bath. After three hours the flask was removed from the oil bath and allowed to cool. Stirring was continued while enough water was added to fill the flask. The resulting solids were collected on a sintered glass frit and subsequently dissolved in 1 liter of methylene chloride. The organic phase was then washed with water (3×1 L) and dried over magnesium sulfate. After filtering over Celite volatiles were removed under reduced pressure to yield 26 g (61%) of yellow-orange solids.

Figure 1:
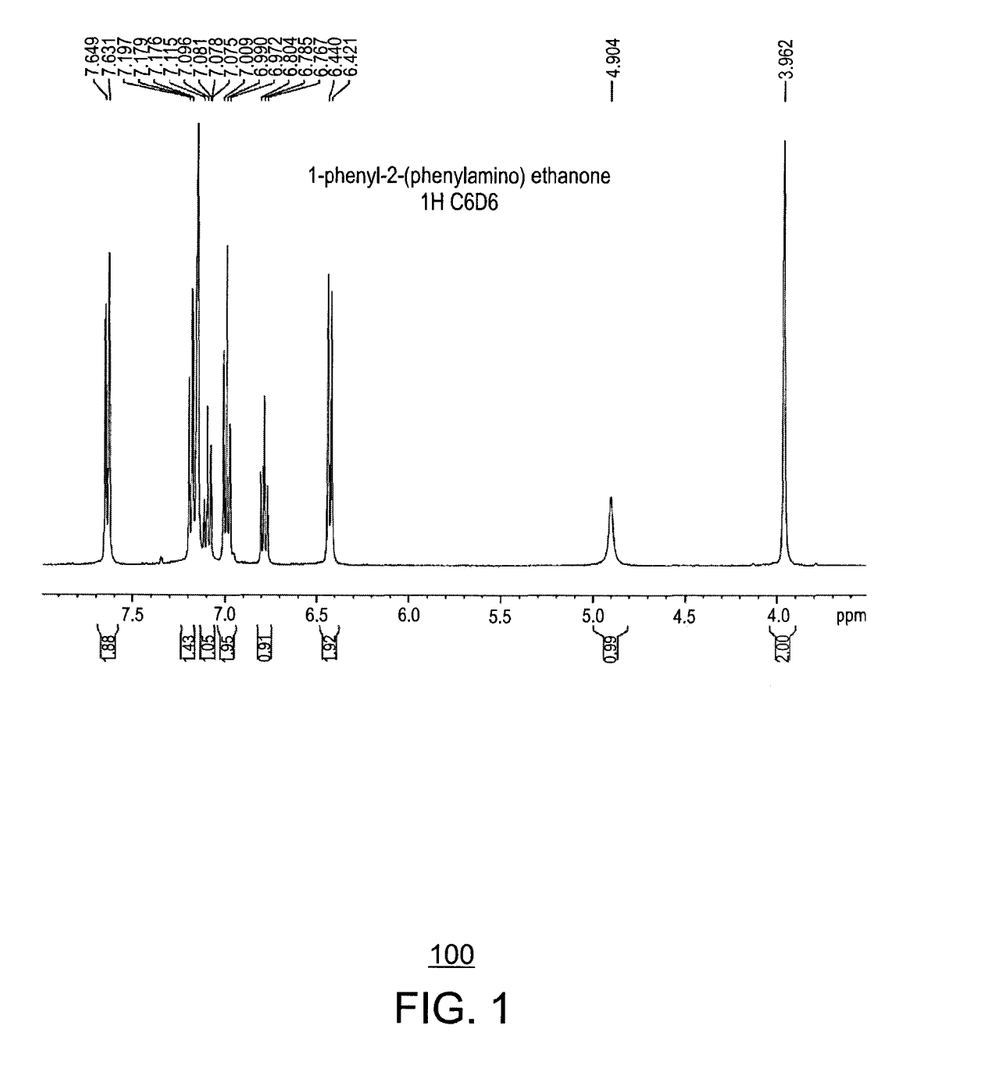
FIG. 1 is a plot of the $^1$H NMR obtained for 1-phenyl-2-(phenylamino)ethanone.

FIG. 1 is a plot 100 of the $^1$H NMR obtained for 1-phenyl-2-(phenylamino)ethanone. The NMR was taken on a 400 MHz instrument in a solution of $C_6D_6$. The crude product was approximately 90-95% pure by $^1$H NMR spectroscopy. The high purity material was obtained from cooling (−35° C.) diethyl ether solutions of the crude product and isolating the resulting solids.

Step 2 of the ligand synthesis was performed using scheme (4).

Preparation of $N^1$-(2-aminoethyl)-$N^2$,1-diphenylethane-1,2-diamine

Figure 2:
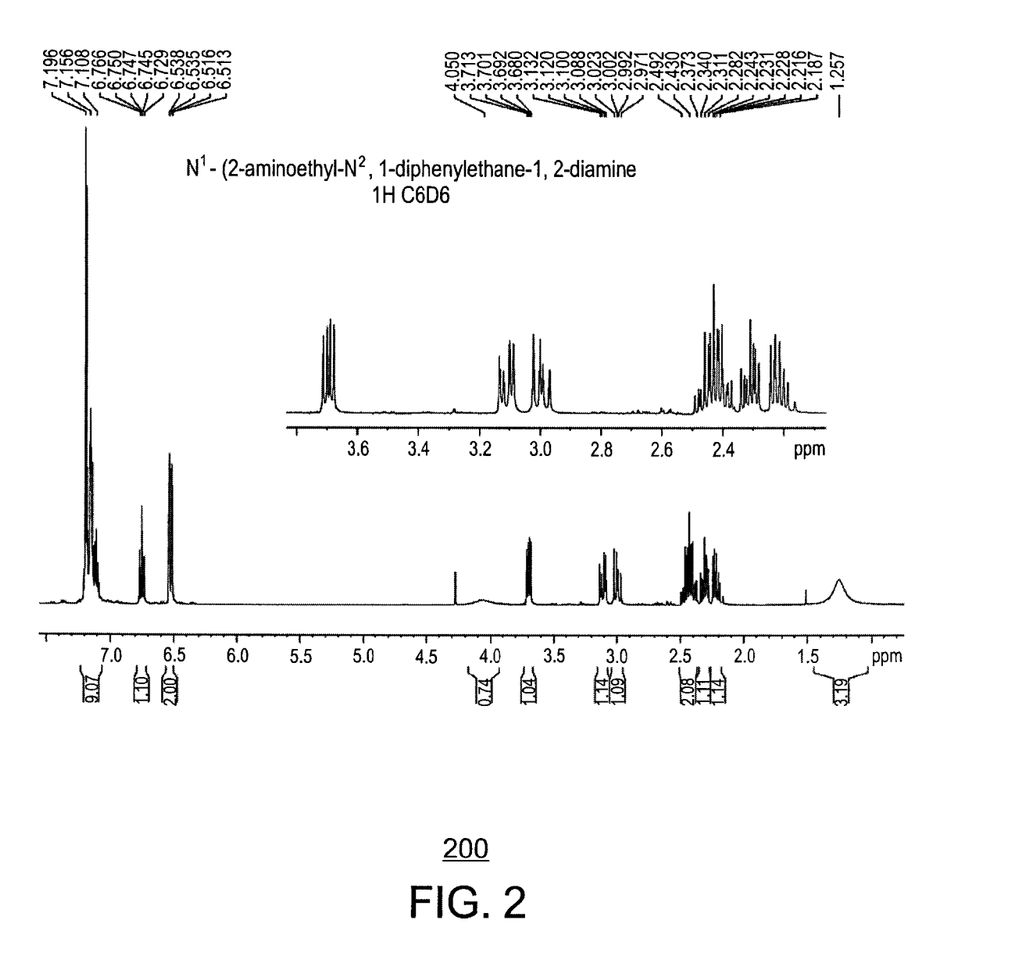
FIG. 2 is a plot of the $^1$H NMR obtained for N1-(2-aminoethyl)-N2,1-diphenylethane-1,2-diamine.

1-phenyl-2-(phenylamino)ethanone (1.63 g, 7.72 mmol) and ethylenediamine (1.39 g, 23.1 mmol) were stirred together in 60 mL of methanol to yield a yellow slurry. Titanium(IV) isopropoxide (2.85 g, 10.0 mmol) was then added dropwise as a neat liquid, resulting in a maroon slurry. After stirring at room temperature for 21 hours the reaction was cooled to 0° C. and sodium borohydride (0.292 g, 7.72 mmol) was added in small portions as a solid. Three hours later the reaction was quenched with 3 mL of water and pumped down. The resulting material was extracted with toluene (60 mL), filtered over Celite, and again pumped down to yield 1.05 g of an orange oil. Purification was accomplished by loading the oil onto a basic alumina plug (a 15 mL sintered glass frit nearly full of solid) as a methylene chloride solution and flushing the plug with additional methylene chloride (20 mL), followed by diethyl ether (20 mL), ethyl acetate (20 mL), and finally methanol (40 mL). The methanol fraction was collected, blown down, and dried under reduced pressure at 40° C. to yield 0.469 g of a viscous orange oil (24%). $^1$H NMR (400 MHz, $C_6D_6$):

FIG. 2 is a plot 200 of the $^1$H NMR obtained for the N1-(2-aminoethyl)-N2,1-diphenylethane-1,2-diamine. The NMR was taken on a 400 MHz instrument in a solution of $C_6D_6$.

Step 3 of the ligand synthesis was performed using scheme (5).

Preparation of ((2-(2-(2,3,4,5,6-pentamethylphenylamido)ethylamine)-2-phenylethyl)(phenyl)amido) ZrBn$_2$: A benzene solution (2 mL) of N$^1$-(2-(2,3,4,5,6-pentamethylphenylamino)ethyl)-N$^2$,1-diphenylethane-1,2-diamine (0.150 g, 0.374 mmol) was added dropwise to a stirring benzene solution (5 mL) of tetrabenzylzirconium (0.170 g, 0.374 mmol). After 2 hours the reaction was lyophilized and the resulting yellow solid was washed with pentane (20 mL) and dried under reduced pressure to yield 0.201 g (80%) of product. The resulting catalyst precursor, ((2-(2-(2,3,4,5,6-pentamethylphenylamido)ethylamine)-2-phenylethyl)(phenyl)amido)ZrBn$_2$ is abbreviated herein as (NNN-Ph)ZrBn$_2$.

Figure 4:
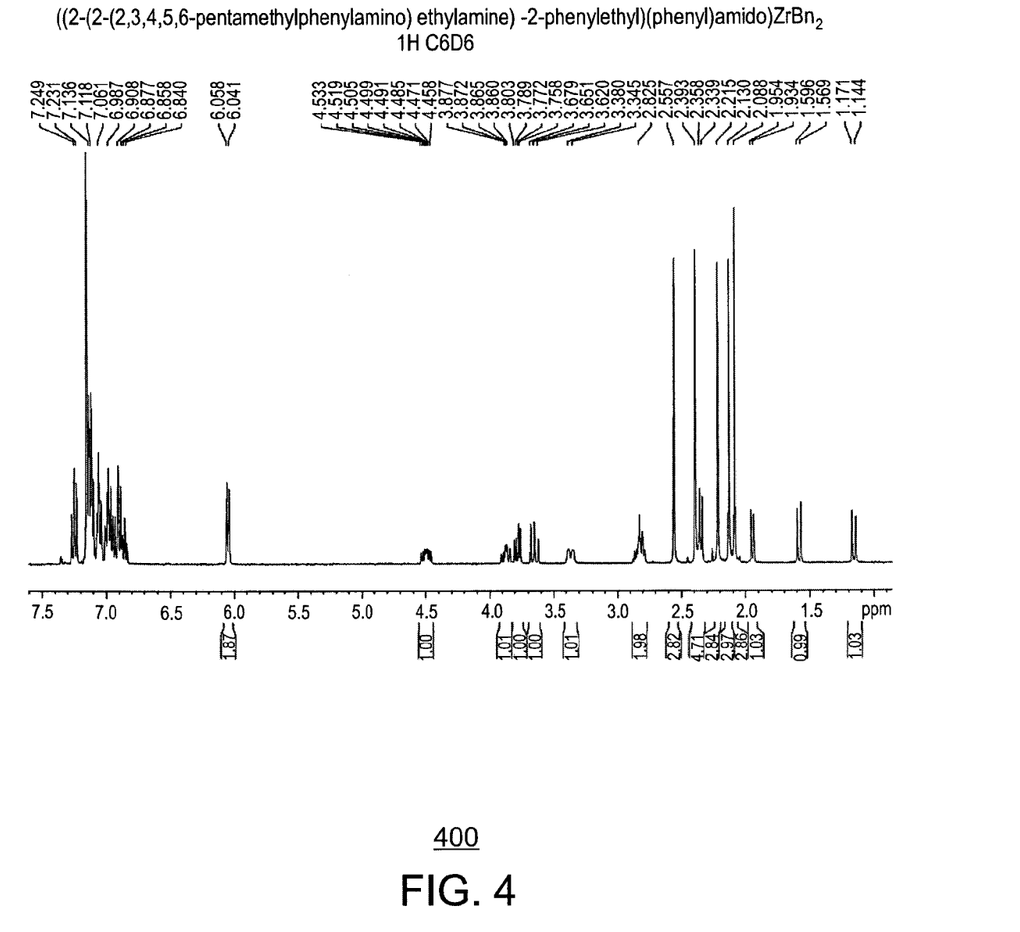
FIG. 4 is a plot of the $^1$H NMR obtained for ((2-(2-(2,3,4,5,6-pentamethylphenylamido)ethylamine)-2-phenylethyl)(phenyl)amido)ZrBn$_2$.

FIG. 4 is a plot of the $^1$H NMR obtained for the (NNN-Ph)ZrBn$_2$. The NMR was taken on a 400 MHz instrument in a solution of C$_6$D$_6$.

High throughput experimentation for catalyst testing.

Ethylene/1-hexene copolymerizations were carried out in a parallel pressure reactor, which is described in U.S. Pat. Nos. 6,306,658, 6,455,316 and 6,489,1681; WO 00/09255; and Murphy et al., *J. Am. Chem. Soc.*, 2003, 125, 4306-4317. A pre-weighed glass vial insert and disposable stirring paddle were fitted to each reaction vessel of the reactor, which contains 48 individual reaction vessels. The reactor was then closed and each vessel was individually heated to a set temperature (usually 85 and/or 100° C.) and pressurized to a pre-determined pressure of ethylene (generally 135 psi). 100 uL of 1-hexene (806 umol) was injected into each reaction vessel. 500 equivalents of MAO were then introduced to each cell to act as a co-catalyst/scavenger. The contents of the vessel were then stirred at 800 rpm. A toluene solution of catalyst (20 nmol) was then added and the volume of the cell made up to 5 mL with isohexane. The reaction was then allowed to proceed until a set time limit (usually 30 min) or until a set amount of ethylene had been taken up by the reaction (ethylene pressure was maintained in each reaction vessel at the pre-set level by computer control). At this point, the reaction was quenched by exposure to air. After the polymerization reaction, the glass vial insert containing the polymer product and solvent was removed from the pressure cell and the inert atmosphere glovebox and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine comonomer incorporation, and by DSC (see below) to determine melting point.

Preparation of N$^1$-(2-(2,3,4,5,6-pentamethylphenylamino)ethyl)-N$^2$,1-diphenylethane-1,2-diamine by Buchwald-Hartwig palladium coupled amination In a drybox, pentamethylbromobenzene (0.417 g, 1.83 mmol) and sodium tert-butoxide (0.441 g, 4.59 mmol) were stirred together in 30 mL of 1,2-dimethoxyethane (DME). N$^1$-(2-aminoethyl)-N$^2$,1-diphenylethane-1,2-diamine was then added dropwise as a 5 mL DME solution. Finally, a pre-mixed DME solution (5 mL) of palladium acetate (4.1 mg, 18.3 μmol) and Josiphos (10.1 mg, 18.3 μmol) was added and the reaction was heated to reflux for 18 hours. Upon cooling, volatiles were removed under reduced pressure and the crude material was extracted with 20 mL of toluene, filtered over Celite, and pumped down to yield a tan solid. Purification on silica gel with diethyl ether as the mobil phase yielded an orange oil (R$_f$=0.57) which, upon washing with fresh pentane, precipitated as a white solid. The white solid was collected and dried to yield 0.240 g of pure product (33%).

Figure 3:
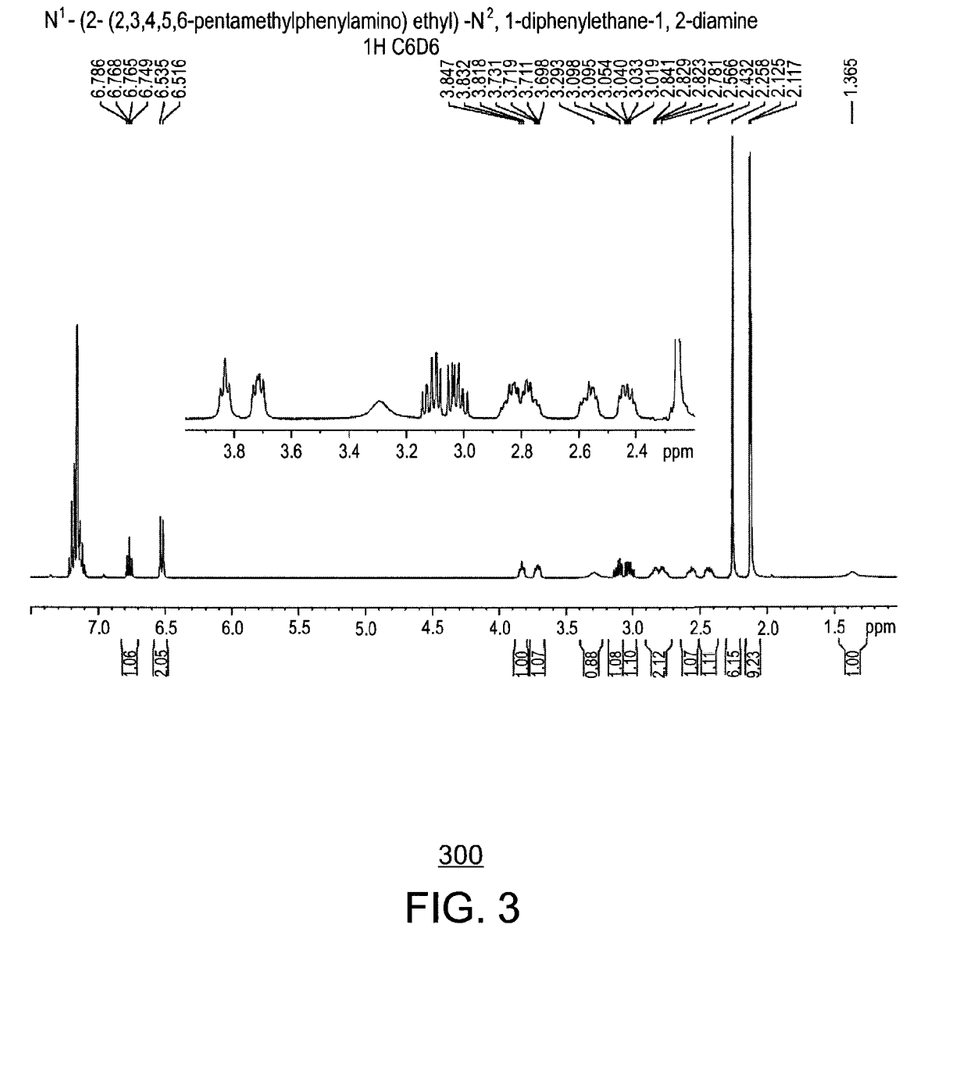
FIG. 3 is a plot of the $^1$H NMR obtained for N1-(2-aminoethyl)-N2,1-diphenylethane-1,2-diamine.

FIG. 3 is a plot of the 1H NMR obtained for the N1-(2-aminoethyl)-N2,1-diphenylethane-1,2-diamine. The NMR was taken on a 400 MHz instrument in a solution of C$_6$D$_6$.

Formation of an exemplary catalyst, ((2-(2-(2,3,4,5,6-pentamethylphenylamido)ethylamine)-2-phenylethyl)(phenyl)amido)ZrBn$_2$ ((NNN-Ph)ZrBn$_2$), was performed using scheme (6).

(6)

+

High temperature size exclusion chromatography was performed using an automated "Rapid GPC" system as described in U.S. Pat. Nos. 6,491,816, 6,491,823, 6,475,391, 6,461,515, 6,436,292, 6,406,632, 6,175,409, 6,454,947, 6,260,407 and 6,294,388. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/min and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution were injected into the system. The concentration of the polymer in the eluent was monitored using an evaporative light scattering detector. The molecular weights obtained are relative to linear polystyrene standards.

The ratio of 1-hexene to ethylene incorporated in the polymers (weight %) was determined by rapid FT-IR spectroscopy on a Bruker Equinox 55+ IR in reflection mode. Samples were prepared in a thin film format by evaporative deposition techniques. Weight % 1-hexene was obtained via measurement of the methyl deformation band at ~1378 $cm^{-1}$. The peak height of this band is normalized by the combination and overtone band at ~4322 $cm^{-1}$, which corrects for path length differences. This method was calibrated using a set of ethylene/1-hexene copolymers with a range of known wt. % 1-hexene content.

TABLE 1

Activity, Molecular Weight, PDI and Comonomer Incorporation Results from High Throughput Catalyst Testing

| Condition | Catalyst | Temp (° C.) | Activity (g/mmol/h/bar) | MW (kDa) | PDI (Mw/Mn) | Comonomer Incorp. (wt %) |
|---|---|---|---|---|---|---|
| A | (NNN-Ph)ZrBn2 | 85 | 14,200 | 204 | 2.3 | 6.2 |
| A | (NNN-Ph)ZrBn2 | 85 | 14,200 | 183 | 2.2 | 5.8 |
| A | (NNN-Ph)ZrBn2 | 85 | 14,900 | 199 | 2.2 | 5.7 |
| A | (NNN-Ph)ZrBn2 | 85 | 15,100 | 183 | 2.2 | 6.0 |
| A | (NNN-Ph)ZrBn2 | 85 | 15,700 | 188 | 2.2 | 5.4 |
| B | (NNN-Ph)ZrBn2 | 100 | 6,300 | 181 | 2.3 | 6.3 |
| B | (NNN-Ph)ZrBn2 | 100 | 7,800 | 170 | 2.3 | 5.8 |
| B | (NNN-Ph)ZrBn2 | 100 | 7,800 | 160 | 2.3 | 6.0 |
| B | (NNN-Ph)ZrBn2 | 100 | 9,800 | 152 | 2.2 | 6.4 |
| B | (NNN-Ph)ZrBn2 | 100 | 10,900 | 165 | 2.2 | 5.3 |

While the foregoing is directed to embodiments of the present invention, other and further embodiments of the invention can be devised without departing from the basic scope thereof, and the scope thereof is determined by the claims that follow.

What is claimed is:

1. A method for forming a polymerization catalyst, comprising:
   reacting a bromoketone compound with an aryl amine compound to form an amide compound, wherein the bromoketone compound has the following formula and the aryl amine compound has the formula: $ArH_2$, wherein R is an aryl group, a substituted aryl group, or an alkyl group comprising 2 to 20 carbons, and Ar is an aryl group or a substituted aryl group;

reacting the amide compound with an ethylene diamine compound, forming a terminal primary amine compound; and
   reacting the terminal primary amine compound with a bromoaryl compound to form a ligand.

2. The method of claim 1, wherein forming the amide compound comprises the reaction:

3. The method of claim 1, wherein forming the terminal amine compound comprises the reaction:

wherein R is an aryl group, a substituted aryl group, or an alkyl group comprising 2 to 20 carbons, and Ar is an aryl group or a substituted aryl group.

4. The method of claim 1, wherein forming the ligand comprises the reaction:

wherein R is an aryl group, a substituted aryl group, or an alkyl group comprising 2 to 20 carbons, Ar is an aryl group, or a substituted aryl group, and Ar' is an aryl group or a substituted aryl group.

5. The method of claim 1, comprising reacting the ligand with a metal compound to form a catalyst.

6. The method of claim 5, wherein forming the catalyst comprises the reaction:

wherein M is a group 4 element, R is an aryl group, a substituted aryl group, or an alkyl group comprising 2 to 20 carbons, Ar is an aryl group or a substituted aryl group, Ar' is an aryl group or a substituted aryl group, and each X individually is a hydride, a methyl group, an alkyl group, a benzyl group, a chloro group, a bromo group, a fluoro group, or an iodo group.

7. The method of claim 5, wherein forming the catalyst comprises the reaction:

8. A method for generating a polyethylene polymer, comprising:
reacting a bromoketone compound with an aryl amine compound to form an amide compound, wherein the bromoketone compound has the following formula and the aryl amine compound has the formula: $ArH_2$,
wherein R is an aryl group, a substituted aryl group, or an alkyl group comprising 2 to 20 carbons, and Ar is an aryl group or a substituted aryl group;
reacting the amide compound with an ethylene diamine compound, forming a terminal primary amine compound;
reacting the terminal primary amine compound with a bromoaryl compound to form a ligand; and
reacting the ligand with a metal compound to form a catalyst precursor; and
activating the catalyst precursor to form an active catalyst; and
reacting the catalyst with at least ethylene to form a polymer.

9. The method of claim 8, wherein the amide compound has the formula:

wherein R is an aryl group, a substituted aryl group, or an alkyl group comprising 2 to 20 carbons, and Ar is an aryl group or a substituted aryl group.

10. The method of claim 8, wherein the terminal amine compound has the formula:

wherein R is an aryl group, a substituted aryl group, or an alkyl group comprising 2 to 20 carbons, and Ar is an aryl group or a substituted aryl group.

11. The method of claim 8, wherein the bromoaryl compound has the formula: Ar'Br, wherein Ar' is an aryl group or a substituted aryl group.

12. The method of claim 8, wherein the ligand has the formula:

wherein R is an aryl group, a substituted aryl group, or an alkyl group comprising 2 to 20 carbons, Ar is an aryl group or a substituted aryl group, and Ar' is an aryl group or a substituted aryl group.

13. The method of claim 8, wherein the catalyst precursor has the formula:

wherein M is a group 4 element, R is an aryl group, a substituted aryl group, or an alkyl group comprising 2 to 20 carbons, Ar is an aryl group or a substituted aryl group, Ar' is an aryl group or a substituted aryl group, and each X is, independently, a hydride, a methyl group, an alkyl group, a benzyl group, an amide group, a chloro group, a bromo group, a fluoro group, or an iodo group.

14. The method of claim 8, comprising forming polymer in a gas phase polymerization reactor.

15. The method of claim 8, comprising forming polymer in a slurry phase polymerization reactor.

16. The method of claim 8, comprising forming a spray dried catalyst.

* * * * *